US012650874B2

(12) United States Patent
Mizunuma et al.

(10) Patent No.: US 12,650,874 B2
(45) Date of Patent: Jun. 9, 2026

(54) CALCULATION PROCESSING SYSTEM, CALCULATION PROCESSING METHOD AND CALCULATION PROCESSING PROGRAM

(71) Applicant: NTT, Inc., Tokyo (JP)

(72) Inventors: Mamoru Mizunuma, Tokyo (JP); Shingo Mineta, Tokyo (JP); Soichi Oka, Tokyo (JP)

(73) Assignee: NTT, INC., Tokyo (JP)

( * ) Notice: Subject to any disclaimer, the term of this patent is extended or adjusted under 35 U.S.C. 154(b) by 526 days.

(21) Appl. No.: 18/251,293

(22) PCT Filed: Nov. 13, 2020

(86) PCT No.: PCT/JP2020/042448
§ 371 (c)(1),
(2) Date: May 1, 2023

(87) PCT Pub. No.: WO2022/102085
PCT Pub. Date: May 19, 2022

(65) Prior Publication Data
US 2023/0409372 A1      Dec. 21, 2023

(51) Int. Cl.
*G06F 9/455*      (2018.01)
*G16H 20/60*      (2018.01)
(52) U.S. Cl.
CPC ......... *G06F 9/45558* (2013.01); *G16H 20/60* (2018.01); *G06F 2009/4557* (2013.01)
(58) Field of Classification Search
None
See application file for complete search history.

(56) References Cited

U.S. PATENT DOCUMENTS 9,928,107 B1 *   3/2018   Vincent ................. G06F 9/5077
2011/0022711 A1   1/2011   Cohn
(Continued)

FOREIGN PATENT DOCUMENTS

JP      2013500518 A   1/2013
JP      2013092951 A   5/2013
JP      2018018340 A   2/2018

OTHER PUBLICATIONS

Distcloud Project Team, "Successful construction of data sharing platform applicable during disasters", Osaka University, Dec. 16, 2013, http://www.osaka-u.ac.jp/ja/news/ResearchRelease/2013/12/20131216_1, 9 pages (with translation), as discussed in the specification.
(Continued)

*Primary Examiner* — Wynuel S Aquino
(74) *Attorney, Agent, or Firm* — Slater Matsil, LLP

(57)      ABSTRACT
A calculation processing system includes: a first processing device including a first computer and a first movement control management device; and a second processing device including a second computer and a second movement control management device, the first processing device and the second processing device are connected with each other, the temperature of a place where the first processing device is installed is higher than the temperature of a place where the second processing device is installed, and the second computer executes calculation in a virtual machine migrated from the first computer, exhausts heat generated in association with the calculation, and transmits a result of the calculation to the first computer.

13 Claims, 5 Drawing Sheets

(56)         References Cited

U.S. PATENT DOCUMENTS

| | | | |
|---|---|---|---|
| 2013/0111492 A1 | 5/2013 | Nojiri et al. | |
| 2014/0303787 A1* | 10/2014 | Struckmeier | F24D 11/005 |
| | | | 700/276 |
| 2015/0143363 A1* | 5/2015 | Gombert | G06F 9/5083 |
| | | | 718/1 |
| 2020/0036785 A1* | 1/2020 | Kandula | H04L 67/1095 |

OTHER PUBLICATIONS

Miyanagi, "Fujitsu and others begin joint demonstration of inter-continental data center collaboration using cold data storage", Impress Watch, Nov. 21, 2016, http://cloud.watch.impress.co.jp/docs/news/1031052.html, 9 pages with translation, as discussed in the specification.

\* cited by examiner

Fig. 2

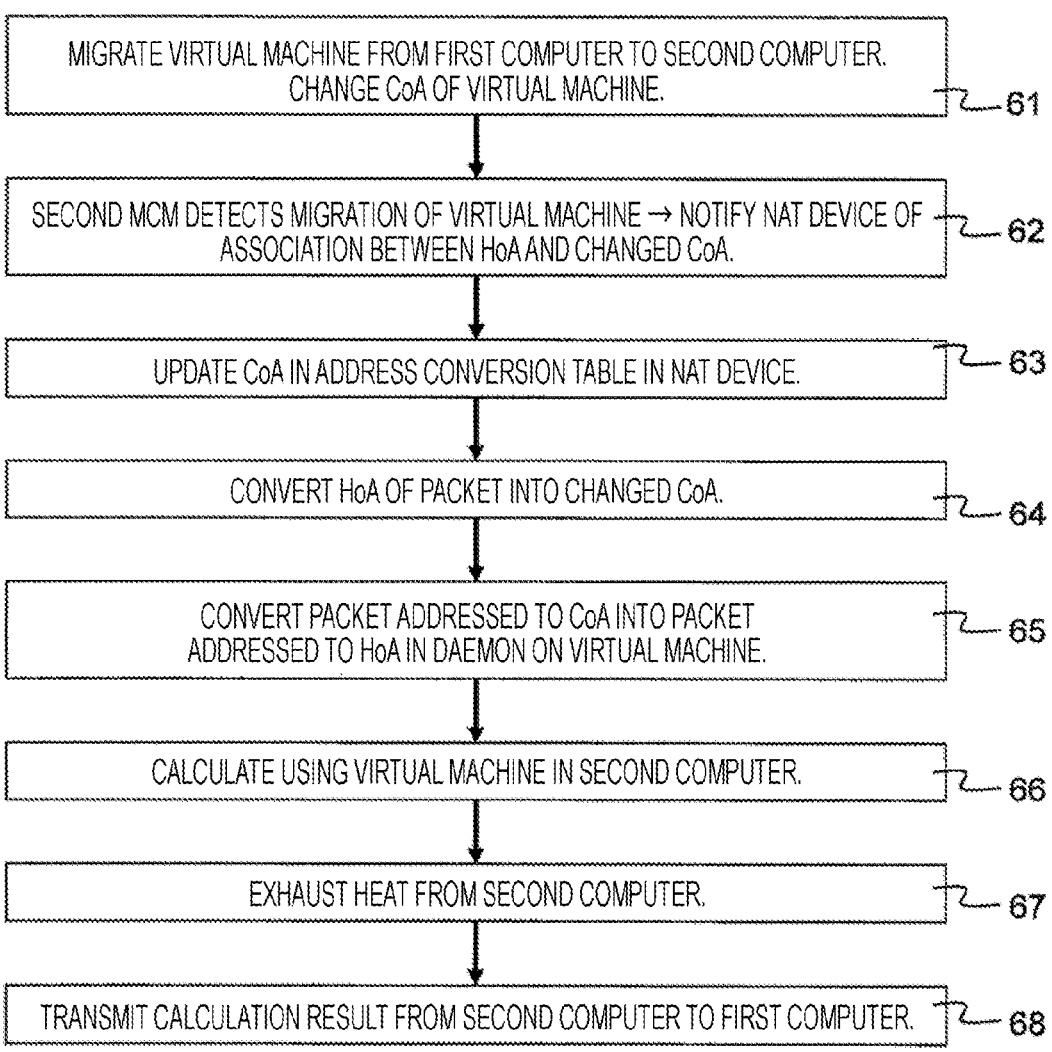

MIGRATE VIRTUAL MACHINE FROM FIRST COMPUTER TO SECOND COMPUTER. CHANGE CoA OF VIRTUAL MACHINE. — 61

SECOND MCM DETECTS MIGRATION OF VIRTUAL MACHINE → NOTIFY NAT DEVICE OF ASSOCIATION BETWEEN HoA AND CHANGED CoA. — 62

UPDATE CoA IN ADDRESS CONVERSION TABLE IN NAT DEVICE. — 63

CONVERT HoA OF PACKET INTO CHANGED CoA. — 64

CONVERT PACKET ADDRESSED TO CoA INTO PACKET ADDRESSED TO HoA IN DAEMON ON VIRTUAL MACHINE. — 65

CALCULATE USING VIRTUAL MACHINE IN SECOND COMPUTER. — 66

EXHAUST HEAT FROM SECOND COMPUTER. — 67

TRANSMIT CALCULATION RESULT FROM SECOND COMPUTER TO FIRST COMPUTER. — 68

Fig. 4

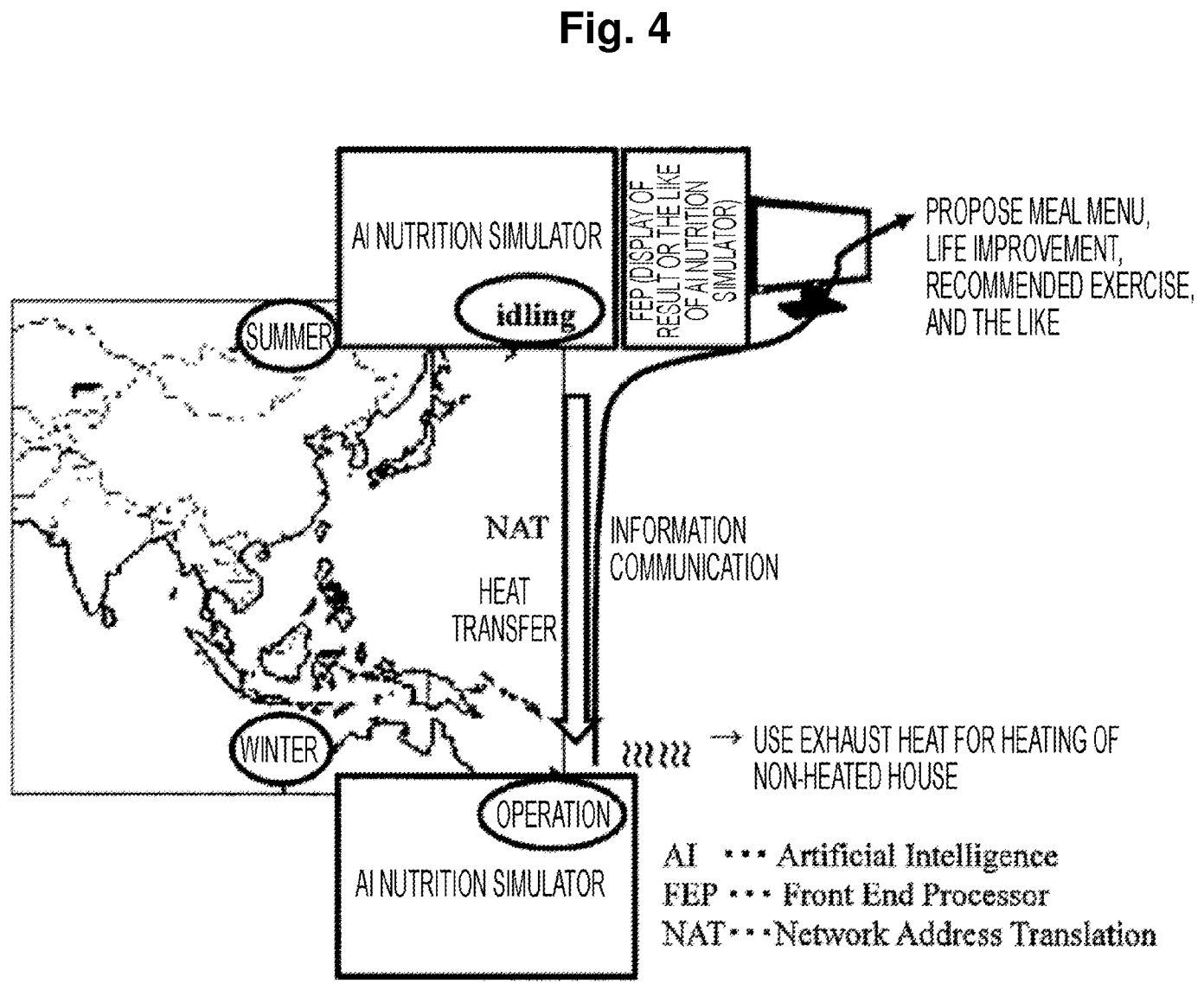

PROPOSE MEAL MENU, LIFE IMPROVEMENT, RECOMMENDED EXERCISE, AND THE LIKE

FEP (DISPLAY OF RESULT OR THE LIKE OF AI NUTRITION SIMULATOR)

AI NUTRITION SIMULATOR idling

SUMMER

INFORMATION COMMUNICATION

NAT

HEAT TRANSFER

WINTER

OPERATION

AI NUTRITION SIMULATOR

→ USE EXHAUST HEAT FOR HEATING OF NON-HEATED HOUSE

AI · · · Artificial Intelligence
FEP · · · Front End Processor
NAT · · Network Address Translation

CALCULATION PROCESSING SYSTEM, CALCULATION PROCESSING METHOD AND CALCULATION PROCESSING PROGRAM

CROSS-REFERENCE TO RELATED APPLICATIONS

This application is a national phase entry of PCT Application No. PCT/JP2020/042448, filed on Nov. 13, 2020, which application is hereby incorporated herein by reference.

TECHNICAL FIELD

The present invention relates to a calculation processing system, a calculation processing method, and a calculation processing program for migrating a virtual machine between computers.

BACKGROUND

In association with the spread and expansion of the Internet based on optical communication, large-scale data centers have been constructed and used in various countries around the world. In a data center, attempts have been made to use exhaust heat of server devices for heating an office provided adjacently, residual heat of a heated swimming pool, or district heating.

On the other hand, in the optical communication technology, high-speed broadband has progressed, and a large amount of data and the like can be instantaneously moved over a global distance (Non Patent Literature 1 and Non Patent Literature 2). For business continuity planning (BCP) or disaster recovery (DR), communication with a latency (communication delay) of approximately several milliseconds is practically used in a data center that secures a backup of data in a data storage distant from each other or provides contents requiring immediate response such as websites or game apps located 500 km or more away from the metropolitan area or Osaka.

Furthermore, due to the problem of global warming, there is a movement to search for conversion from fossil fuel-derived heat sources to renewable energy for heating of houses and the like. Under such circumstances, there is also an attempt to construct a "non-heated house" which ultimately improves heat insulation performance, uses people, home appliances, hot water supply, and the like that live or are used in the house as a heat source, and maintains a living appropriate temperature without releasing the heat to the outside of the house. Although there seems to be a tendency in practice to think that it is more economical to make some compromises on the heat insulation performance and plan to use appropriate heating and cooling equipment, the progress of heat insulation technology in the construction field is reaching a level that makes it possible to pass winter without heating.

CITATION LIST

Non Patent Literature

Non Patent Literature 1: http://cloud.watch.impress.co.jp/docs/news/1031052.html (Joint Demonstration Experiment of Inter-Continental Data Center Cooperation Utilizing Cold Data Storage)

Non Patent Literature 2: http://www.osaka-u.ac.jp/ja/news/ResearchRelease/2013/12/20131216_1 (Construction of Data Sharing Platform Applicable at the Time of Disaster).

SUMMARY

Technical Problem

Although effective utilization of exhaust heat (=energy saving) has been actively studied in order to solve environmental and energy problems, it is generally difficult to use heat at a remote place, and there is a strict restriction particularly on the utilization of low-temperature exhaust heat. Moreover, although the inter-season heat transfer in which cold energy in winter is used for cooling in summer and hot energy in summer is used for heating in winter is a "dream technology", only extremely limited practical examples have been reported.

On the other hand, the present day is regarded as an information explosion era, and the amount of information distribution is rapidly increasing mainly on the Internet. Accordingly, electric power required for a server and for cooling the server and low-temperature exhaust heat in a data center or the like cause disadvantages such as an increase in environmental load, and in many cases, methods for effective use are difficult. It is an object to effectively utilize low-temperature exhaust heat by moving a site (IT device, server, and storage) handling such information processing or an information processing process over a long distance by optical communication to realize suppression of oil consumption.

Solution to Problem

In order to solve the above-described problems, a calculation processing system according to embodiments of the present invention is characterized by including: a first processing device including a first computer and a first movement control management device; and a second processing device including a second computer and a second movement control management device, in which the first processing device and the second processing device are connected with each other, a temperature of a place where the first processing device is installed is higher than a temperature of a place where the second processing device is installed, and the second computer executes calculation in a virtual machine migrated from the first computer, exhausts heat generated in association with the calculation, and transmits a result of the calculation to the first computer.

Moreover, a calculation processing method according to embodiments of the present invention includes: a step of migrating a virtual machine from a first computer to a second computer installed in a place at a temperature lower than a temperature of a place where the first computer is installed, and changing a care of address of the virtual machine; a step of detecting, by a second movement control management device, migration of the virtual machine, and notifying an NAT device of an association between a home address and a changed care of address; a step of updating an address to the changed care of address in an address conversion table of the NAT device; a step of converting a home address of a packet transmitted to the virtual machine of the second computer into the changed care of address; a step of changing the changed care of address of the packet after being transmitted to the virtual machine to the home address; a step of calculating, by the second computer, data included in the packet by using the virtual machine; a step of exhausting heat generated in association with calculation by the second computer; and a step of transmitting a result of the calculation from the second computer to the first computer.

Moreover, a calculation processing program according to embodiments of the present invention is capable of causing a calculation processing system to function, the calculation processing system including a first computer, a first movement control management device, a second computer installed in a place at a temperature lower than a temperature of a place where the first computer is installed, a second movement control management device, and an NAT device connected with the first processing device and the second processing device, the calculation processing method being characterized by causing the calculation processing system to execute processing including: a step of migrating a virtual machine from the first computer to the second computer and changing a care of address of the virtual machine; a step of detecting, by the second movement control management device, migration of the virtual machine and notifying the NAT device of an association between a home address and a changed care of address; a step of updating an address to the changed care of address in an address conversion table of the NAT device; a step of converting a home address of a packet transmitted to the virtual machine of the second computer into the changed care of address; a step of changing the changed care of address of the packet after being transmitted to the virtual machine to the home address; a step of calculating, by the second computer, data included in the packet by using the virtual machine; a step of exhausting heat generated in association with calculation by the second computer; and a step of transmitting a result of the calculation from the second computer to the first computer.

Advantageous Effects of Embodiments of Invention

According to embodiments of the present invention, it is possible to provide a calculation processing system, a calculation processing method, and a calculation processing program capable of effectively using exhaust heat associated with calculation processing.

BRIEF DESCRIPTION OF THE DRAWINGS

FIG. 2 is a flowchart for explaining a calculation processing method according to the first embodiment of the present invention.

FIG. 4 is a diagram for explaining a second practical example of the present invention.

DETAILED DESCRIPTION OF ILLUSTRATIVE EMBODIMENTS

First Embodiment

A calculation processing system according to a first embodiment of the present invention will be described with reference to FIGS. 1 and 2.

<Configuration of Calculation Processing System>

Figure 1:
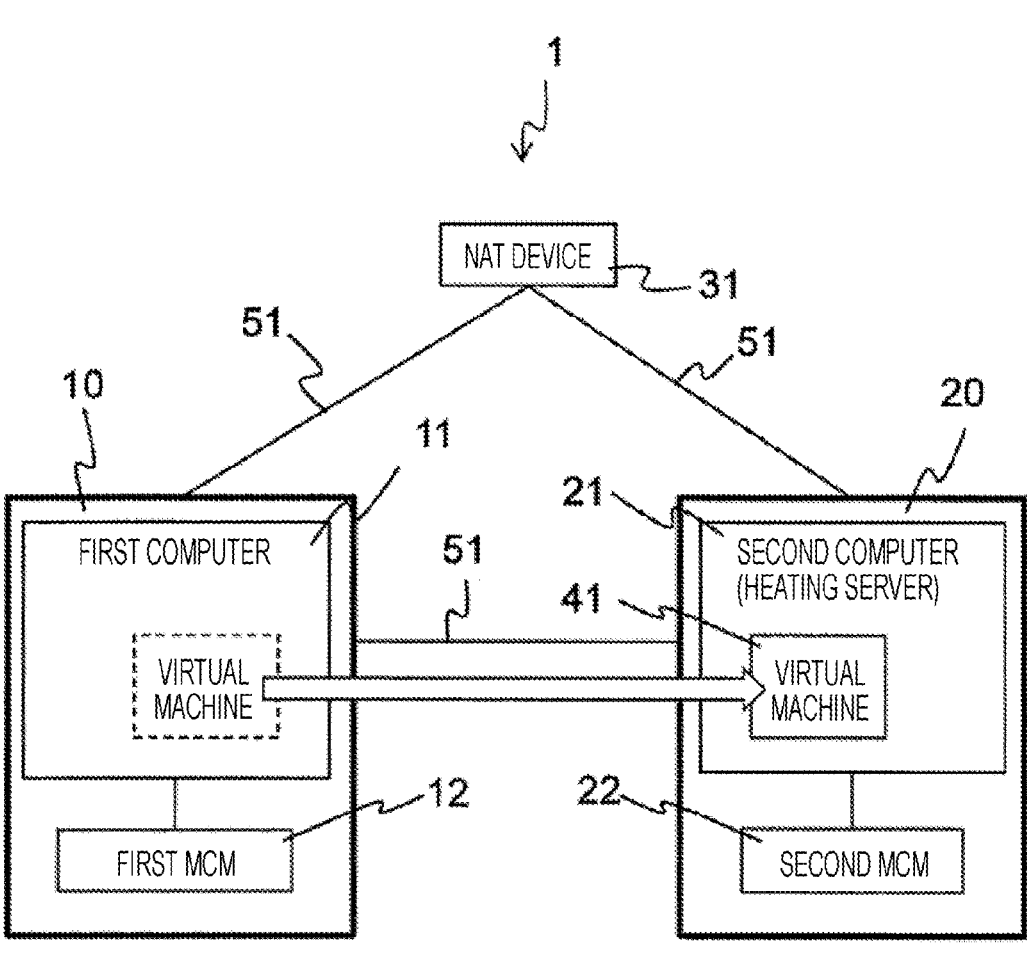
FIG. 1 is a schematic diagram illustrating a configuration of a calculation processing system according to a first embodiment of the present invention.

As illustrated in FIG. 1, a calculation processing system 1 according to the present embodiment includes a first processing device 10, a second processing device 20, and a network address translation (NAT) device 31 connected with the processing device 10 and the processing device 20. Communication lines 51 are used for connection between the devices, and each communication line is an optical fiber, an electric cable, or the like.

The processing device 10 includes a first computer 11 and a first movement control management device (MCM, Migration Control Manager) 12.

Similarly, the processing device 20 includes a second computer (heating server) 21 and a second movement control management device (MCM) 22.

The second computer (heating server) 21 has a heating function in addition to a calculation function. In a non-heated house, a heat source for maintaining the temperature in the house is heat generated by a resident, and exhaust heat of home appliances, cooking, baths, and the like. Since the heat generation by the resident is approximately 100 W/person and the exhaust heat of the bath is 100 W or more, it is sufficiently useful as heating in the house if approximately 100 to 500 W can be used as the exhaust heat of the heating server 21.

On the other hand, since a multi-core CPU with low power consumption has a heat generation amount of approximately 150 W at present, the heating server 21 has a sufficient function when calculation processing using one to several CPUs of such a degree is performed. Calculation processing performed by the second computer (heating server) 21 will be described later.

Moreover, NAT is a technology to be used by a user who uses a private address to convert the private address into an external network address, and the NAT device 31 that performs address conversion is installed between internal and external networks.

The NAT device 31 holds a table in which addresses before and after conversion are associated with each other, and performs one-to-one address conversion from a certain address (private address) to another address (global address) in response to a request from a user.

The NAT device 31 holds an address management table in which addresses before and after conversion are associated with each other.

A virtual machine 41 executes calculation processing in a computer. In the present embodiment, the virtual machine 41 is migrated from the first computer 11 to the second computer 21, and executes calculation processing in the second computer 21.

In the first computer 11 and the second computer 21, there are an IP address that is permanently used by the user for the virtual machine 41, and an IP address to which the virtual machine 41 is temporarily allocated in the migration destination second processing device 20. Hereinafter, the former is referred to as a home address (HoA), and the latter is referred to as a care of address (CoA).

A CoA is allocated to the virtual machine 41 in the migration destination second processing device 20, while the virtual machine 41 uses an HoA. Therefore, the virtual machine 41 has a daemon that is a program for converting each address. A packet transmitted to the virtual machine 41 addressed to a CoA is converted to a packet addressed to an HoA.

The first MCM 12 and the second MCM 22 manage the HoA and the CoA of the virtual machine 41.

<Operation of Calculation Processing System>

An operation of the calculation processing system 1 will be described below. In the calculation processing system according to the present practical example, in the winter season, since a normal heating demand is in a region including a computer (first computer 11), heat generation associated with calculation processing of the computer (first computer 11) may be used in, for example, a room or a conference room in a business office, a room or a bedroom in a general house, or the like. On the other hand, in the summer season, heating demand generally shifts to cooling demand. At this time, heat generation (exhaust heat) associated with calculation processing performed by the computer (first computer 11) becomes unnecessary, or rather causes a disadvantage.

In this case, it is possible to collectively move (live migration) the virtual machine (VM) 41 operating on the computer (first computer 11) to another computer (second computer 21) while keeping the software running on the virtual machine 41 in the execution state by the NAT technology in the layer 2 (data link layer) of the open system interconnect (OSI) reference model of the Internet. (Taka-hashi, Takeshita, Ishii, Okamoto, and Yamanaka: "A Study on Virtual Machine Migration Scheme for Achieving Sun-Tracking Data Center", IEICE Technical Report, PN, Pho-tonic Network 110 (264), 29-34, 2010-10-25.)

At this time, the virtual machine 41 as the movement destination is set to operate on a computer (second computer 21) installed in a region in the winter season in another continent. Alternatively, it may be moved (follow the moon) to a computer (second computer 21) installed in a cool region such as a highland in the middle of the night from a city where solar heat is sufficient in the daytime (e.g., from Yokohama in the daytime in the winter season to Nagano or Sapporo), or installed in a city where heating demand increases in the night or from sun-declining time to happy evening dinner or going-to-bed time from a city where solar heat is sufficient in the daytime (e.g., from Istanbul in September to December→Tokyo, etc.). In this way, the surplus cooling power required to operate the computer (first computer 11) during the hot summer season is migrated to the remote region where the heating demand exists, so that the exhaust heat energy can be effectively used.

In a simple trial calculation, where the power consumption for submarine optical communication is 1, approxi-mately 20 of computer exhaust heat can be transferred. Moreover, a delay time of inter-continent communication is approximately 0.2 seconds, and the migration destination may be anywhere on the earth as long as service processing regardless of real-time properties is used.

<Calculation Processing Method>

A calculation processing method according to the present embodiment will be described with reference to a flowchart illustrated in FIG. 2.

The NAT device 31 in the present embodiment is provided with a function of accepting an update request of the address conversion table from the outside.

Moreover, the migration destination computer (second computer) 21 is determined in consideration of the operating situation of the computer. Alternatively, it may be deter-mined in advance.

First, the virtual machine 41 is migrated from the first computer 11 to the second computer 21. In association with the migration of the virtual machine 41, the CoA of the virtual machine 41 is changed (step 61).

Next, the second MCM 22 detects the migration of the virtual machine 41 and notifies the NAT device 31 of the association between the HoA and the changed CoA (step 62).

Next, the NAT device 31 updates (rewrites) the CoA in the address conversion table into the changed CoA (step 63).

In a case where a packet having data is transmitted from the user to the second computer 21, an HoA, which is a destination address in the packet, of the packet is converted into the updated CoA on the basis of the address conversion table in the NAT device 31 (step 64). As a result, the packet becomes a packet addressed to the CoA and is transmitted to the second computer 21.

Next, the daemon on the virtual machine 41 in the second computer 21 converts (reversely converts) the packet trans-mitted to the virtual machine 41 addressed to a CoA into a packet addressed to an HoA (step 65).

Next, data included in the packet is calculated by the second computer 21 using the virtual machine 41 (step 66).

Next, heat generated in association with calculation is exhausted from the second computer 21 (step 67).

Finally, the calculation result is transmitted from the second computer to the first computer (step 68).

According to a calculation processing system according to the present embodiment, exhaust heat associated with cal-culation processing can be effectively used as a heat source for living residence in two stages (subsequent to calculation processing) in a highly airtight and highly heat-insulated house such as a non-heated house. As a result, it is possible to suppress the consumption of fossil fuel by using the exhaust heat of the energy source once used for necessary calculation processing from heat derived from petroleum, natural gas, or the like which has been required in the related art.

First Practical Example

Figure 3:
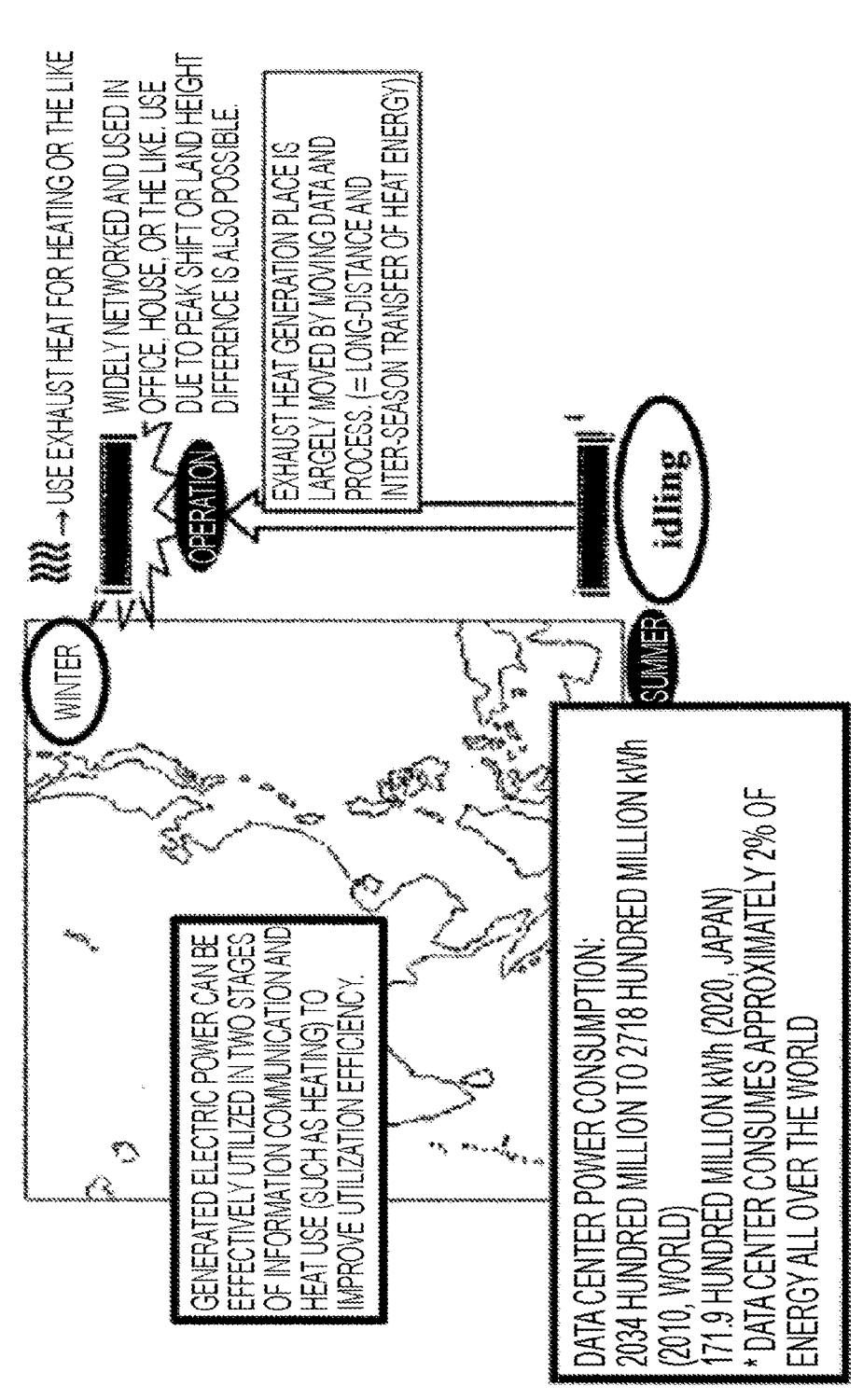
FIG. 3 is a diagram for explaining a first practical example of the present invention.

A calculation processing system according to a first practical example of the present invention will be described with reference to FIG. 3. In the present practical example, migration of the virtual machine 41 from the first computer 11 installed in a summer region (e.g., Australia) to the second computer (heating server) 21 installed in a winter region (e.g., Japan) will be described as an example.

In a conventional calculation processing system, exhaust heat generated by calculation in a computer in Australia is not effectively used in Australia in the summer season.

On the other hand, in a calculation processing system according to the present practical example, the virtual machine 41 is migrated from the first computer 11 installed in Australia in the summer season to the second computer (heating server) 21 installed in Japan in the winter season. As a result, the data and the calculation processing (process) are moved from Australia in the summer season to Japan in the winter season, and the exhaust heat generation site is moved. That is, the heat energy can be transferred between seasons over a long distance.

Exhaust heat generated by calculation processing in the virtual machine 41 migrated to Japan in the winter season is used for heating or the like. When the virtual machine 41 is widely networked and used in an office, a house, or the like to be used, it is also possible to use the virtual machine due to a peak shift, a land height difference, or the like.

As described above, the generated electric power can be effectively utilized in two stages of information communi-cation and heat use such as heating to improve utilization efficiency.

Although the migration of the virtual machine 41 from Australia in the summer season to Japan in the winter season is described as an example in the present practical example, the present invention is not limited thereto, and the virtual machine 41 may be migrated from Japan in the summer season to Australia in the winter season. Moreover, the virtual machine 41 may be migrated between regions having a temperature difference in Japan, for example, between Okinawa and Hokkaido. All that is required is that the virtual machine 41 is migrated from a computer installed in a high temperature region or place to a computer installed in a low temperature region or place.

Second Practical Example

A calculation processing system according to a second practical example of the present invention will be described with reference to FIG. 4. In the present practical example, an artificial intelligence (AI) nutrition simulator is applied to the virtual machine 41 in the calculation processing system according to the first embodiment.

In the calculation processing system according to the present practical example, an AI nutrition simulator is migrated as the virtual machine 41 from the first computer 11 installed in Japan in the summer season to the second computer (heating server) 21 installed in Australia in the winter season, and calculation processing is executed in Australia. The exhaust heat generated by this calculation processing is used for heating or the like in Australia in the winter season. In this way, heat transfer from Japan in the summer season to Australia in the winter season becomes possible.

Next, the result of the calculation processing is transmitted to Japan via an information communication network, and the calculation result is obtained in Japan.

As described above, the generated electric power can be effectively utilized in two stages of information communication and heat use such as heating to improve utilization efficiency.

Details of the AI nutrition simulator will be described below. Although any program in any field is basically considered to be applicable as a calculation task executed (including migration (exhaust heat transfer)) by the heating server 21 used in embodiments of the present invention, artificial intelligence nutrition science (AI nutrition science) is considered to be preferable from the viewpoint that the user can obtain benefit at home by installation at home.

First, an information collection device such as a sensor or a camera is installed near a dining table or the like at home, and a dish before a meal taken by each person is photographed, and contents of the meal ingested by each person are analyzed and stored by the artificial intelligence. Moreover, daily activities (commutation, work, exercise state) of each member are inputted and stored separately using means such as a medical interview. In this manner, information on daily activities including meals of the user is inputted and stored, and a packet including such information as data is transmitted to the heating server (second computer) 21.

Next, the artificial intelligence which operates in the heating server 21 precisely simulates how the ingested nutrients are metabolized in the body and accumulated and consumed in the body of each person on the basis of medical and molecular nutritional knowledge, and proposes daily life actions such as a meal menu, life improvement proposal, and recommended exercise to a family member on the basis of the analysis result.

Moreover, nutrition may differ depending on when the nutrition is ingested, and it is important to incorporate the concept of chrono-nutrition from the viewpoint that the timing of ingestion, such as morning, daytime, or night, is important (Ando: "Expected to open up new possibilities of nutrition science and health management by utilization of future simulation science of life science developed by bio-supercomputing", Bio-Supercomputing News Letter Vol. 4, http://www.csrp.riken.jp/BSNewsLetters/BSNvol4-1102/JP/special2.html).

An execution program should be adopted if it is possible to perform time-series simulation on what kind of nutrients ingested when offers what kind of effects to a person, and a database based on medical and molecular nutritional knowledge may be provided and means for reference may be used.

On the other hand, there is also a problem of malnutrition. Even in Japan and the like where dietary insufficiency is generally not considered to be a problem, a case of malnutrition due to, for example, dietary restrictions of elderly people, lifestyle-related diseases, or the like has been reported. In such a case, it is preferable to provide the heating server 21 that can provide an accurate meal recommendation menu and an accurate simulator of insufficient nutrients or amounts and can be used for health promotion.

Although it is normal at present to maintain health by ingesting medicine to restore a biological balance when suffering from a disease, it is considered that it is possible to maintain a healthy mind and body for a long time only with healthy meals without relying on medicine and supplements (health supplement) when the AI nutrition science (artificial intelligence and nutrition) simulator is completed although it is necessary to provide tailored nutrition (meal menu), and this can contribute to a healthy and long life society.

As described above, by operating the present simulator on the heating server 21 and operating the simulator at the optimum position (site) on the earth between seasons as described above, it is considered that this contributes to energy saving and eventually contributes to prevention of global warming. As illustrated in FIG. 4, only the calculation processing process with large exhaust heat is migrated to a region in the winter season, and a front end processor (FEP) and the like related to display are continuously operated near the user. Note that when summer and winter are reversed, the reverse operation of FIG. 4 is performed.

Although migration of the virtual machine 41 from Japan in the summer season to Australia in the winter season is described as an example in the present practical example, the present invention is not limited thereto, and the virtual machine 41 may be migrated from Australia in the summer season to Japan in the winter season. Moreover, the virtual machine 41 may be migrated between regions having a temperature difference in Japan, for example, between Okinawa and Hokkaido. All that is required is that the virtual machine 41 is migrated from a computer installed in a high temperature region or place to a computer installed in a low temperature region or place.

As described above, a calculation processing system according to a practical example of the present invention relates to a technology for effectively using heat exhausted from a computer by moving a calculation processing process or a site over a long distance by optical communication to a position (region) where heat demand in the winter season (or night highland) is strong, such as between continents in different seasons.

Figure 5:
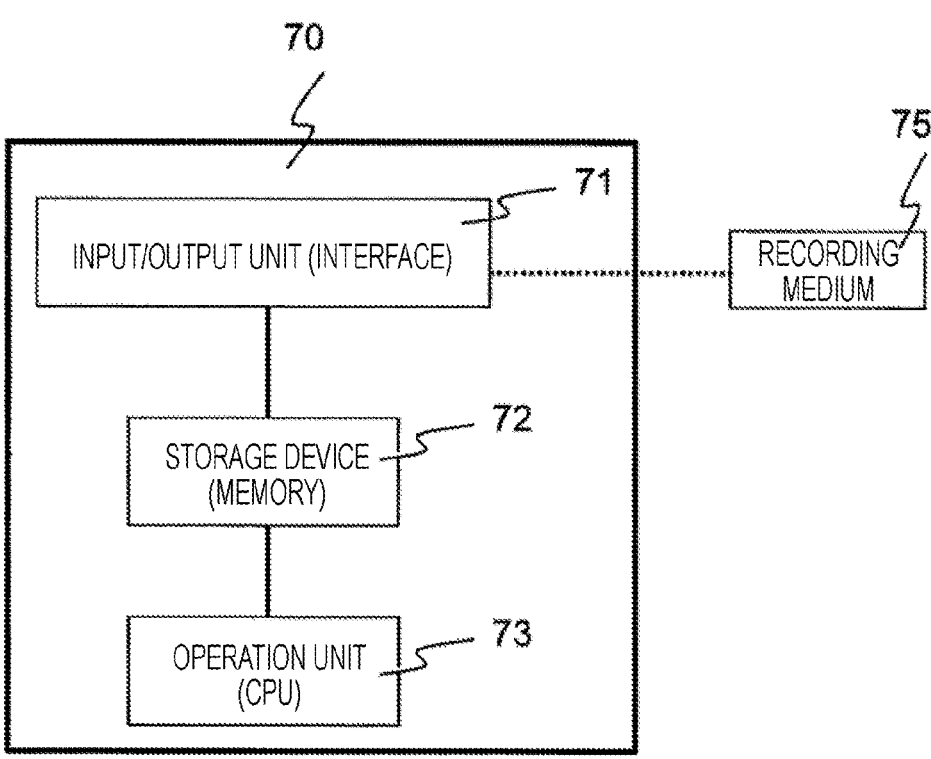
FIG. 5 is a diagram illustrating a configuration example of a computer according to an embodiment of the present invention.

FIG. 5 illustrates a configuration example of a computer 70 in a calculation processing system according to an embodiment and a practical example of the present invention. The calculation processing system can be implemented by a computer including a central processing unit (CPU) 73, a storage device (storage unit) 72, and an interface device 71, and a program for controlling these hardware resources. The CPU 73 executes processing in an embodiment of the present invention according to a calculation processing program stored in the storage device 72. Thus, the calculation processing program causes the calculation processing system to function.

In the calculation processing system according to an embodiment of the present invention, the computer 70 may be provided inside the device, or at least some of the functions of the computer may be implemented using an external computer. Moreover, the storage unit may also use the storage medium 75 outside the device, and a calculation processing program stored in the storage medium 75 may be read and executed. The storage medium 75 includes various magnetic recording media, magneto-optical recording media, CD-ROMs, CD-Rs, and various memories. Moreover, the calculation processing program may be supplied to a computer via a communication line such as the Internet.

Although an example of the structure and the like of each component has been described in the embodiment of the present invention regarding the configuration and the like of the calculation processing system, the present invention is not limited thereto. All that is required is that the function of the calculation processing system is exhibited and effects thereof are achieved.

INDUSTRIAL APPLICABILITY

Embodiments of the present invention can be applied to a communication network between data centers for energy saving or the like.

REFERENCE SIGNS LIST

1 Calculation processing system
10 First processing device
11 First computer
12 First movement control management device
20 Second processing device
21 Second computer
22 Second movement control management device
31 NAT device
41 Virtual machine
51 Communication line.

The invention claimed is:

1. A calculation processing system characterized by comprising: a first processing device including a first computer and a first movement control management device; a second processing device including a second computer and a second movement control management device, and a NAT device connected with the first processing device and the second processing device, the NAT device having an address conversion table configured to manage a home address and a care of address of a virtual machine, wherein the first processing device and the second processing device are connected with each other, wherein a temperature at a location of the first processing device is higher than a temperature at a location of the second processing device, wherein the second computer is configured to execute calculation in the virtual machine migrated from the first computer, exhaust heat generated in association with the calculation, and transmit a result of the calculation to the first computer, wherein the second movement control management device is configured to detect migration of the virtual machine from the first computer to the second computer and notify the NAT device of an association between the home address and a changed care of address, wherein the NAT device is configured to convert the home address of a packet transmitted to the virtual machine into the changed care of address, and wherein the virtual machine includes a daemon configured to convert the changed care of address of the packet to the home address after the packet is received by the virtual machine.

2. The calculation processing system according to claim 1 wherein:

an artificial intelligence nutrition simulator is applied to the virtual machine, data included in the packet is information on daily activities of a user, and the artificial intelligence nutrition simulator is configured to:

calculate a situation including metabolism, accumulation, and consumption of nutrients ingested by the user; and propose actions in daily life.

3. A calculation processing method comprising:

a step of migrating a virtual machine from a first computer to a second computer, the second computer being installed in a place at a temperature lower than a temperature of a place where the first computer is installed, and changing a care of address of the virtual machine;

a step of detecting, by a second movement control management device, migration of the virtual machine, and notifying an NAT device of an association between a home address and a changed care of address;

a step of updating an address to the changed care of address in an address conversion table of the NAT device;

a step of converting a home address of a packet transmitted to the virtual machine of the second computer into the changed care of address;

a step of changing the changed care of address of the packet after being transmitted to the virtual machine to the home address;

a step of calculating, by the second computer, data included in the packet using the virtual machine;

a step of exhausting heat generated in association with calculating the data included in the packet by the second computer; and a step of transmitting a result of calculating the data included in the packet from the second computer to the first computer, wherein:

an artificial intelligence nutrition simulator is applied to the virtual machine, data included in the packet is information on daily activities of a user, and the artificial intelligence nutrition simulator is configured to:

calculate a situation including metabolism, accumulation, and consumption of nutrients ingested by the user; and propose actions in daily life.

4. A non-transitory computer-readable storage device storing a calculation processing program that when executed by one or more processors, cause the one or more processors to execute:

a step of migrating a virtual machine from a first computer to a second computer and changing a care of address of the virtual machine, wherein the second computer is installed in a second location having a lower temperature than a first location where the first computer is installed, and wherein a calculation processing system comprises the first computer, a first movement control management device, the second computer, a second movement control management device, and an NAT device;

a step of detecting, by the second movement control management device, migration of the virtual machine and notifying the NAT device of an association between a home address and a changed care of address;

a step of updating an address to the changed care of address in an address conversion table of the NAT device;

a step of converting a home address of a packet transmitted to the virtual machine of the second computer into the changed care of address;

a step of changing the changed care of address of the packet after being transmitted to the virtual machine to the home address;

a step of calculating, by the second computer, data included in the packet using the virtual machine;

a step of exhausting heat generated in association with calculating the data included in the packet by the second computer; and a step of transmitting a result of calculating the data included in the packet from the second computer to the first computer, wherein:

an artificial intelligence nutrition simulator is applied to the virtual machine, data included in the packet is information on daily activities of a user, and the artificial intelligence nutrition simulator is configured to:

calculate a situation including metabolism, accumulation, and consumption of nutrients ingested by the user; and propose actions in daily life.

5. The calculation processing system according to claim 1, wherein the second computer is configured as a heating server having a heating function in addition to a calculation function.

6. The calculation processing system according to claim 1, wherein the virtual machine is migrated from the first computer to the second computer based on a seasonal temperature difference between a location of the first computer and a location of the second computer, such that exhaust heat generated by the second computer is used for heating in a region where the second computer is installed during a winter season.

7. The calculation processing system according to claim 1, wherein the first processing device and the second processing device are connected via a communication line comprising an optical fiber.

8. The calculation processing method according to claim 3, wherein the step of migrating the virtual machine comprises performing live migration while keeping software running on the virtual machine in an execution state.

9. The calculation processing method according to claim 3, wherein the step of exhausting heat comprises providing the exhausted heat as a heat source for a residential building.

10. The calculation processing method according to claim 3, wherein the first computer is installed in a summer region and the second computer is installed in a winter region, such that the virtual machine is migrated based on a seasonal temperature difference to transfer heat energy between seasons.

11. The non-transitory computer-readable storage device according to claim 4, wherein the step of migrating the virtual machine comprises performing live migration while keeping software running on the virtual machine in an execution state.

12. The non-transitory computer-readable storage device according to claim 4, wherein the step of exhausting heat comprises providing the exhausted heat as a heat source for a residential building.

13. The non-transitory computer-readable storage device according to claim 4, wherein the first computer is installed in a summer region and the second computer is installed in a winter region, such that the virtual machine is migrated based on a seasonal temperature difference to transfer heat energy between seasons.

* * * * *